(12) United States Patent
Pieper et al.

(10) Patent No.: US 11,439,464 B2
(45) Date of Patent: Sep. 13, 2022

(54) APPLIANCE FOR CONVEYING A CATHETER, LIGHT GUIDE OR CABLE IN A CONTROLLED MANNER

(71) Applicants: Karl Pieper, Niederlenz (CH); Thilo Schmuck, Schongau (CH)

(72) Inventors: Karl Pieper, Niederlenz (CH); Thilo Schmuck, Schongau (CH)

(*) Notice: Subject to any disclaimer, the term of this patent is extended or adjusted under 35 U.S.C. 154(b) by 901 days.

(21) Appl. No.: 16/313,936

(22) PCT Filed: Jun. 21, 2017

(86) PCT No.: PCT/EP2017/065305
§ 371 (c)(1),
(2) Date: Jun. 19, 2019

(87) PCT Pub. No.: WO2018/001836
PCT Pub. Date: Jan. 4, 2018

(65) Prior Publication Data
US 2020/0038106 A1 Feb. 6, 2020

(30) Foreign Application Priority Data

Jun. 28, 2016 (CH) .................... 00823/2016

(51) Int. Cl.
*A61B 18/24* (2006.01)
*A61M 25/01* (2006.01)
(Continued)

(52) U.S. Cl.
CPC ......... *A61B 18/24* (2013.01); *A61M 25/0113* (2013.01); *A61B 2018/00404* (2013.01);
(Continued)

(58) Field of Classification Search
CPC .............. A61M 25/01; A61M 25/0105; A61M 25/0113; A61M 25/0116; A61M 25/0169;
(Continued)

(56) References Cited

U.S. PATENT DOCUMENTS 5,190,538 A * 3/1993 Hussein ................ A61B 18/24
606/15
5,346,498 A * 9/1994 Greelis .............. A61M 25/0119
606/108
(Continued)

FOREIGN PATENT DOCUMENTS

NL         1019350 C2      5/2003
WO      93020876 A1     10/1993
(Continued)

OTHER PUBLICATIONS

International Search Report; PCT Application No. PCT/EP2017/065305; dated Oct. 20, 2017.
(Continued)

*Primary Examiner* — Ahmed M Farah
(74) *Attorney, Agent, or Firm* — Polsinelli PC

(57) ABSTRACT

The device serves for the controlled conveying of a cable. The device has a housing, having a cover plate, on which are externally mounted a drive wheel and contact wheel which can be radially pressed onto the drive wheel, between which the cable can be clamped. The cable can be conveyed by means of the drive wheel being driven by a drive unit in the interior of the housing. The rotational motion of the drive wheel is guided through a stationary light barrier by means of a counting disc, running synchronously therewith and having radial slots or holes in the circumferential area, for determining the motion and rotational speed of the drive wheel. The cover plate and the housing can be sterilized. The drive unit in the interior of the housing is not sterilizable, yet is completely enclosed by the sterilized housing and cover plate.

12 Claims, 9 Drawing Sheets

(51) Int. Cl.
*A61B 18/00* (2006.01)
*A61B 18/22* (2006.01)

(52) U.S. Cl.
CPC ............... *A61B 2018/00619* (2013.01); *A61B 2018/2222* (2013.01); *A61B 2018/2238* (2013.01); *A61M 2205/3327* (2013.01); *A61M 2205/3365* (2013.01); *A61M 2205/8206* (2013.01)

(58) Field of Classification Search
CPC ...... A61M 25/0172; A61M 2025/0177; A61M 2205/3327; A61M 2205/3369; A61M 2205/8206; A61B 18/22; A61B 2018/2238; A61B 18/24; A61B 2018/3365; A61B 2018/00404; A61B 2018/00589; A61B 2018/0063
USPC .................................................. 606/13–15, 7
See application file for complete search history.

(56) References Cited

U.S. PATENT DOCUMENTS

| | | | | |
|---|---|---|---|---|
| 6,171,234 B1* | 1/2001 | White | ............. | A61M 25/09041 600/102 |
| 6,398,755 B1* | 6/2002 | Belef | ........................ | A61B 8/12 604/95.01 |
| 9,782,564 B2* | 10/2017 | Zirps | .................. | A61M 25/0113 |
| 2006/0276775 A1* | 12/2006 | Rosenberg | ........ | A61B 17/00234 606/1 |
| 2008/0097476 A1* | 4/2008 | Peh | ........................ | A61B 34/20 606/130 |
| 2010/0249601 A1* | 9/2010 | Courtney | .............. | A61B 5/6852 600/463 |
| 2015/0297864 A1* | 10/2015 | Kokish | .............. | A61M 25/0113 604/95.04 |
| 2019/0083755 A1* | 3/2019 | Castro | ................ | A61M 25/0113 |

FOREIGN PATENT DOCUMENTS

| | | | | |
|---|---|---|---|---|
| WO | WO-9320876 A1 * | 10/1993 | ......... | A61B 1/00147 |
| WO | 2012037213 A1 | 3/2012 | | |
| WO | WO-2012037213 A1 * | 3/2012 | ............. | A61B 34/30 |
| WO | 2018001836 A1 | 1/2018 | | |

OTHER PUBLICATIONS

English Translation of International Search Report; PCT Application No. PCT/EP2017/065305; dated Oct. 20, 2017.
Written Opinion of PCT Application No. PCT/EP2017/065305; dated Oct. 20, 2017.
English Language Abstract of NL1019350; Retreived From www.espacenet.com on Dec. 26, 2018.

* cited by examiner

APPLIANCE FOR CONVEYING A CATHETER, LIGHT GUIDE OR CABLE IN A CONTROLLED MANNER

CROSS-REFERENCE TO RELATED APPLICATIONS

This application is a national stage entry of PCT/EP2017/065305 filed Jun. 21, 2017, which claims priority to Swiss patent application 00823/2016 filed on Jun. 28, 2016, the contents of each are hereby incorporated by reference in their entirety.

BACKGROUND

This invention relates to a device for retracting a catheter in the form of a light guide, that is a fiber optic cable, specifically from a patient into which the catheter is inserted. The device, however, can also be used for any situation in which an also differently disposed catheter, a light guide or a fiber optic cable or also an other cable is to be conveyed at a certain speed in a precisely controlled and monitored manner.

A particular case, which here was based on statement of the object, is briefly explained hereinafter. Veins are blood vessels which transport the used, oxygen-depleted blood from the tissue back to the heart. In order to cope with this transport even against gravity, the veins are equipped in the extremities with venous valves which have a valve function and thus prevent blood from flowing back into the veins. These veins in the legs and arms of humans run partly within a muscle, but partly also in the surrounding tissue. While those within a muscle cannot expand excessively, this is the case with those in soft tissue. Many people develop so-called varicose veins mainly on their legs. These are pathologically dilated veins which have lost the ability to close the venous valves. This leads to a backward flow of blood in these pathologically altered veins, which therefore lose their transport function and accumulate the blood back into the tissue. This is usually accompanied by a deterioration in blood circulation and often causes discomfort. It is estimated that 25% of people in the western world will need to have their veins operated on at least once during their lifetime. Until recently, this was done in most cases by removing the affected vein sections. In the last two decades, however, newer methods have been developed in which at least the main vein, the so-called saphenous vein, is no longer removed, but left in the body and is closed instead. In this connection, catheters which close the veins using thermal energy have become the most widespread. There are various catheter models on the market which use different energies to generate the heat which ultimately welds the vein. Catheters which use laser light as an energy source have found widespread use. These catheters are inserted into the vein and placed in an ultrasound-guided manner exactly in the venous segment to be treated. The vein is then injected, likewise in an ultrasound-guided manner, with a cooled liquid, which ensures that the vein wall to be treated lies directly against the laser catheter and, apart from that, that the surrounding tissue is protected from the laser energy. After activation of the laser, the catheter is retracted at an even speed millimeter by millimeter. The energy to be used for this purpose is calculated before the procedure on the basis of the vein diameter measured by ultrasound. To ensure that the calculated energy is correctly transferred to the vein wall, the catheter should be retracted very carefully and at a uniform speed, otherwise the energy applied to a particular venous segment would be either too high or too low. In the first case, this can lead to a perforation of the vein or, in the second case, to a missing closure of the vein.

At its front end, the catheter it is equipped with a prism, which ensures that the laser is deflected on all sides by approx. 90° and thus radiates around the axis of the light guide. This allows it to apply its energy all around to the tissue in the vein. If water is simultaneously injected into the tissue from the outside around the circumferential area of the vein, this creates a support pressure around the vein. It is radially compressed on all sides and the laser energy allows the inside of the vein to be welded and thus closed. This is referred to as a phlebosclerosation. While the laser is active, the catheter must be slowly retracted from the vein as uniformly as possible at a speed of approx. 1 mm/s. For welding of a vein or varicose vein 600 mm long, one therefore takes 600 seconds or 10 minutes for the retracting. The extracting is a delicate task for the operating surgeon, which up to now has to be done by hand. If the catheter is not pulled out of the vein at a completely uniform speed, local burning of the tissue may occur if the speed is too slow, and incomplete welding or possibly no welding at all if the speed is too fast. From the prior art a device is known from NL 1 019 350 for conveying of a catheter. The catheter is guided between two rollers having parallel axles, which rotate in opposite directions, wherein one roller is pressed against the other by spring force, so that the catheter is clamped between them. US patent application US 2014/0296633 A1 relates to a device for an endoscope. The endoscope is likewise guided between two rollers having parallel axles, which rotate in opposite directions, wherein one roller is pressed against the other by spring force, so that the catheter is clamped between them. WO 00/18463 shows a device for conveying a catheter for imaging purposes. This device also works on the basis that the catheter is guided between two rollers with parallel axes, which rotate in opposite directions. EP 1 442 720 shows an apparatus for maneuvering flexible catheters in cardiovascular systems. This catheter is also moved between two rollers. The Japanese publication JP 09000492 shows a device for the introducing and extracting of an endoscope, wherein this is moved by means of two counter-rotating rollers. In all these publications, not a word is said about the problem that these devices are to be operated in an operating room and must therefore be completely sterile or have to be sterilized again after each use.

SUMMARY

Hence the object of this invention is to create a device which relieves the surgeon of this delicate and tedious work and enables a continuous, uniformly slow and motorized extraction of such a sweat catheter from a vein. In the process, the device should be able to transport the welding catheter at an adjustable speed and with constant conveying force, preferably by pulling, wherein the device should, however, also be able to thrust the catheter or a similar cable. The device should also ensure that if for any reason conveyance the fiber optic cable is stopped, the laser is immediately shut down to prevent local burns. Finally, the device should make it possible to record the traveled conveying length and also allow a manual stop with simultaneous switch-off of the laser at any time. A particular challenge for the design of such a device is that it must be used in the operating room in the vicinity of the patient's body and must therefore be completely sterile, or it must be sterilizable from application to application, i.e. all external parts must be able to withstand a temperature of up to 180° C., as it occurs in a sterilizer or autoclave, without damage.

This task is solved by a device to controlled conveying of a cable in the form of a catheter having a light guide or a glass fiber or of an electric cable or of a cable-like tubelet which comprises a drive wheel and an pressing wheel which can be pressed radially onto said drive wheel, between which the cable to be conveyed can be clamped, so that it is conveyable by the drive of the drive wheel of a drive unit having an appurtenant control device, and electronic controls and the rotational motion and rotational speed of the drive wheel are measurable by means of a measuring device, wherein this device characterized in that it is designed in three parts, having firstly a cover plate which can be sterilized to at least 180° C. and on which are externally mounted the drive wheel and the contact wheel outside which can be radially pressed onto said drive wheel, secondly a non-sterilizable drive unit having an electronic control, an electric motor, a reduction gear and a power supply, and thirdly a box-shaped housing which can be sterilized to at least 180° C. and into which the drive unit can be completely inserted and can be closed sterilely with the cover plate so that the appliance is completely sterile on outside on all sides, and an appurtenant control device which can be connected to the sterilized appliance via an electric cable.

BRIEF DESCRIPTION OF THE DRAWINGS

With reference to the drawings, an exemplary execution of the device is described in more detail and the functions of the individual components are explained.

There is shown.

During a phlebosclerosation, the doctor pushes a fiberglass cable approx. 1.2 mm thick from bottom to top into the leg vein. If this is positioned correctly, a diode laser with a power of approx. 8 watts and a wavelength of 1470 nm is switched on and remains burning for approx. 3 seconds on the spot. Thereupon the fiber cable is extracting from the vein with an activated laser at a constant speed of about 1 mm/s, so that the vein is sclerosed. The problem for the doctor is now to extract the fiber cable at as uniform a speed as possible for a period of 10 minutes, for example. In phlebosclerosation, the laser power or transport speed is usually adapted to the diameter of the vein. More power is supplied in the upper leg area than in the lower area. Therefore, the process is divided into three different phlebosclerosation sequences, for example. The doctors determine the adjustable laser power/transport speed using a simple formula. The total duration of the phlebosclerosation sequences can be set by means of a preset timer. The present device should now extract this fiber optic cable from the vein purely mechanically at a uniform speed. In case of irregularities or after the end of the program, an acoustic signal should be emitted.

Figure 1:
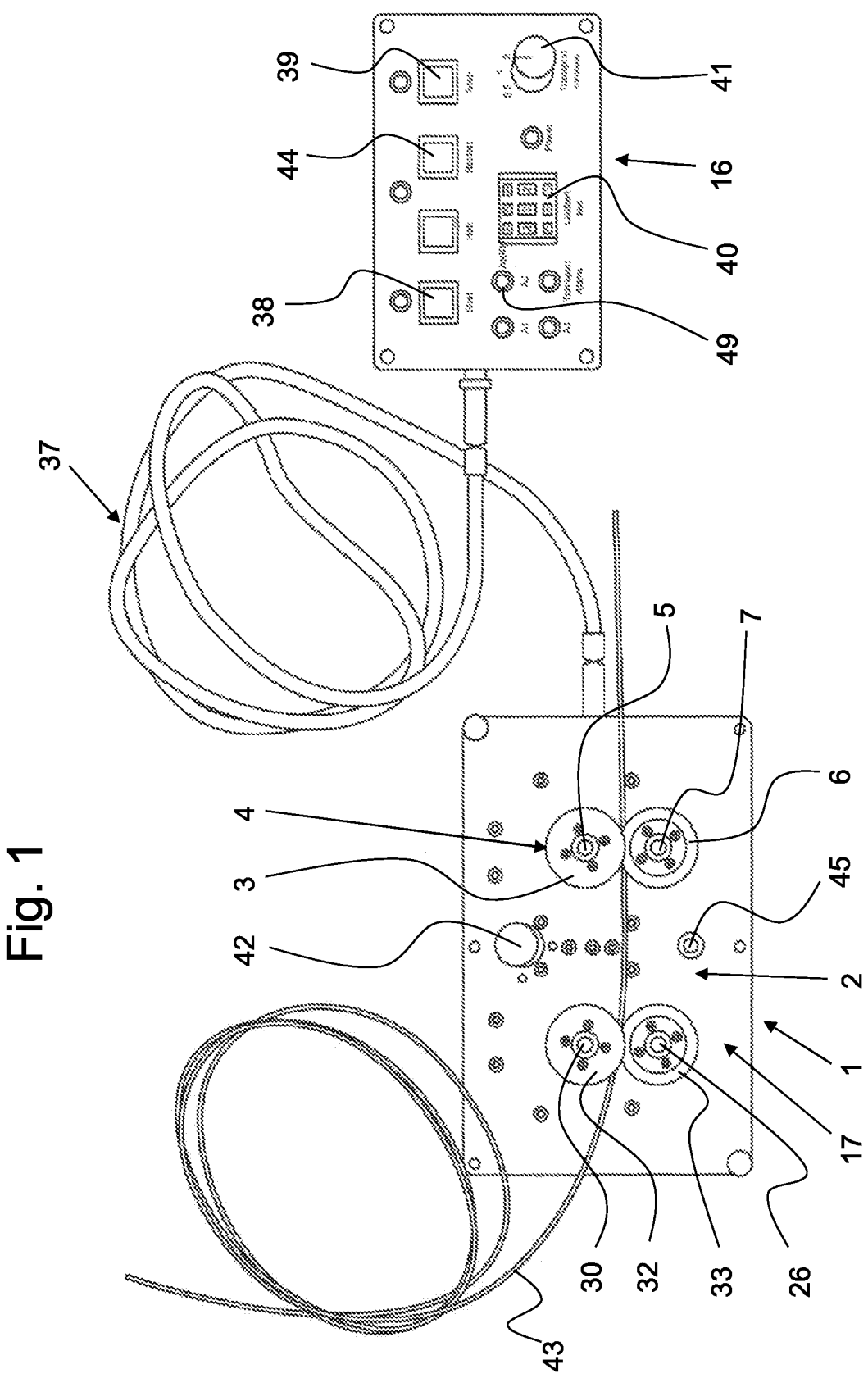
FIG. 1: The device for the controlled conveying of a catheter, light guide or cable with its appurtenant control device and a clamped fiber optic cable.

FIG. 1 shows such a device with its associated control device 16 viewed from above. The device consists of a housing 1, a removable drive unit accommodated therein, and a cover plate 17, with which the housing 1 can be closed from above. The image shows the outer side 2 of the unit or the cover plate 17. The fiber optic cable 43 to be conveyed passes through two pairs of wheels 32, 33 and 3, 6 which are arranged on top of the cover plate 17 and whose axles or shafts 26, 30; 5, 7 pass through the cover plate 17 into the interior of the housing 1. First, the fiber optic cable 43 is passed between the two wheels 32 and 33, which serve to determine the conveying speed, namely between a measuring wheel 32 with a receiving groove for receiving the fiber optic cable 43 rotating outside in its circumferential surface and an appurtenant contact wheel 33, which fits into this groove and which is mounted displaceably by hand against spring force with its axis or shaft 26 in radial direction away from the axis or shaft 30 of the measuring wheel 32. When the two wheels 32, 33 are distanced from each other in this way, the fiber cable 43 can be inserted between them, and when the contact wheel 33 is again released, the fiber cable 43 is pressed into the groove in the circumferential surface of the measuring wheel 32. In the same way, the shaft 7 of the contact wheel 6, visible in the image further to the right, can be moved by hand in the radial direction with respect to the shaft 5 of the drive wheel 3 away from its shaft 5 in order to allow the insertion of the fiber optic cable 43 between the two wheels 3, 6. Afterwards the axle or shaft 7 of the contact wheel 6 is released and it is from now on pressed with spring force onto the circumferential surface of the drive wheel 3, so that the fiber cable 43 clamped in between can be conveyed by the drive wheel 3. For this purpose, the drive wheel 3 may have a circumferential surface 4 with a groove recessed in it having a knurled groove base in order to improve the traction. The rotary knob 42 on the cover plate 17 serves as the main switch for the drive unit below this cover plate 17, and 45 shows a ready light. A multicore electric cable 37 leads to the associated control device 16 with its various organs. On its upper side, one recognizes a start button 38, a stop button 39 and a re-start button 44. Marked with 40, a counter having a reset button indicates the conveying length traveled by the fiber cable 43 as measured by the measuring wheel 32. The conveying speed can be regulated or set using the rotary knob 41.

Figure 2:
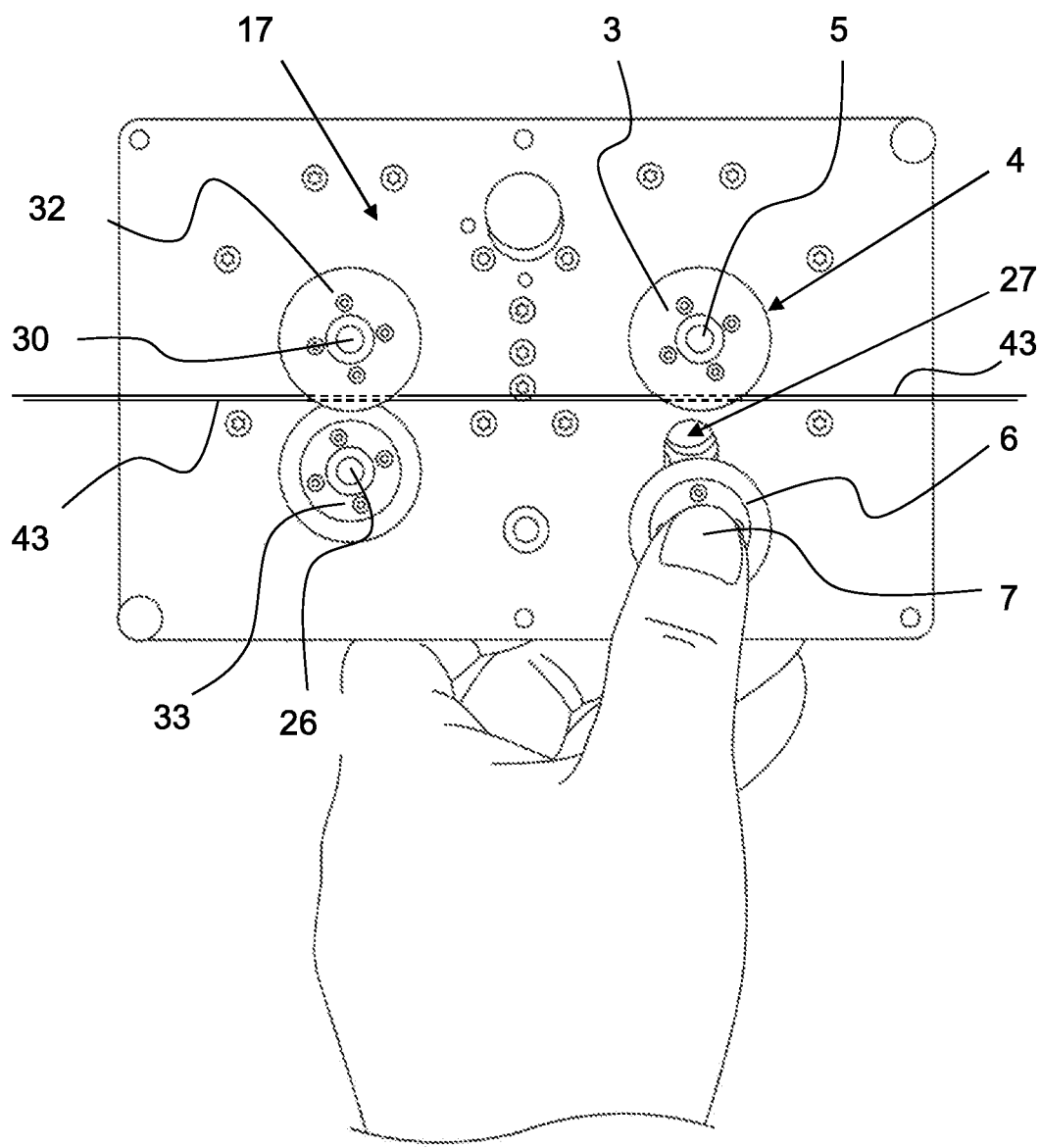
FIG. 2: The cover plate of the device having the drive wheel and measurement wheel as well as the contact wheels viewed from above.

FIG. 2 shows the cover plate 17 of the device in a separate and enlarged illustration. On the left, the measuring wheel 32 with its shaft 30 can be seen and the contact wheel 33 with its shaft 26 for this measuring wheel 32. The contact wheel 33 can be moved away from the measuring wheel 32 in a radial direction against a spring force, wherein the axles or shafts 30, 26 of the two wheels 32, 33 always remain parallel to each other. The displacement path is long enough to create a gap between the wheels 32, 33 so that the fiber optic cable 43 can be placed between this gap in the groove running in the circumferential surface of the measuring wheel 32. Afterwards the contact wheel 33 is again relieved and presses with its spring force on the fiber optic cable lying in the groove. In the same way, the contact wheel 6 in the image can be moved with one finger further to the right of the drive wheel 3 against a spring force, as shown in the image. Its shaft 7 is mounted in a displaceable slide and can be moved along the recess 27 in the cover plate 17. In the case of a displacement as shown, the fiber optic cable between the two wheels 3.6 can be placed in the groove in the circumferential surface 4 of the drive wheel 3 and afterwards the contact wheel 6 presses the fiber optic cable into this groove because of the acting spring force. The drive wheel 6 can have a knurling in its groove to improve traction to the fiber optic cable.

Figure 3:
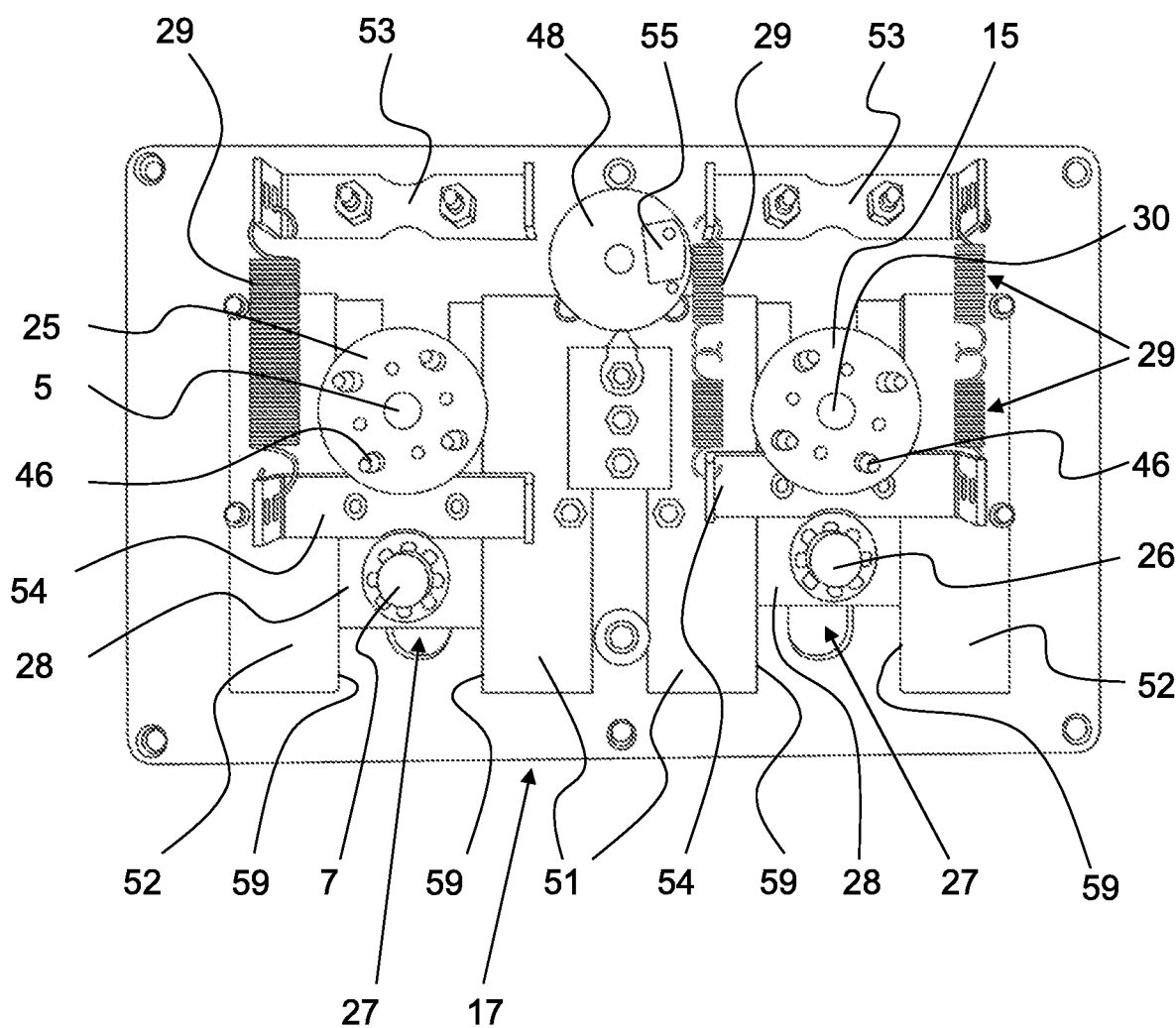
FIG. 3: The underside of the cover plate with the transmission wheels and the slides, in which the contact wheels are displaceable in radial direction against spring force of the drive wheel or pick-up wheel.
Figure 4:
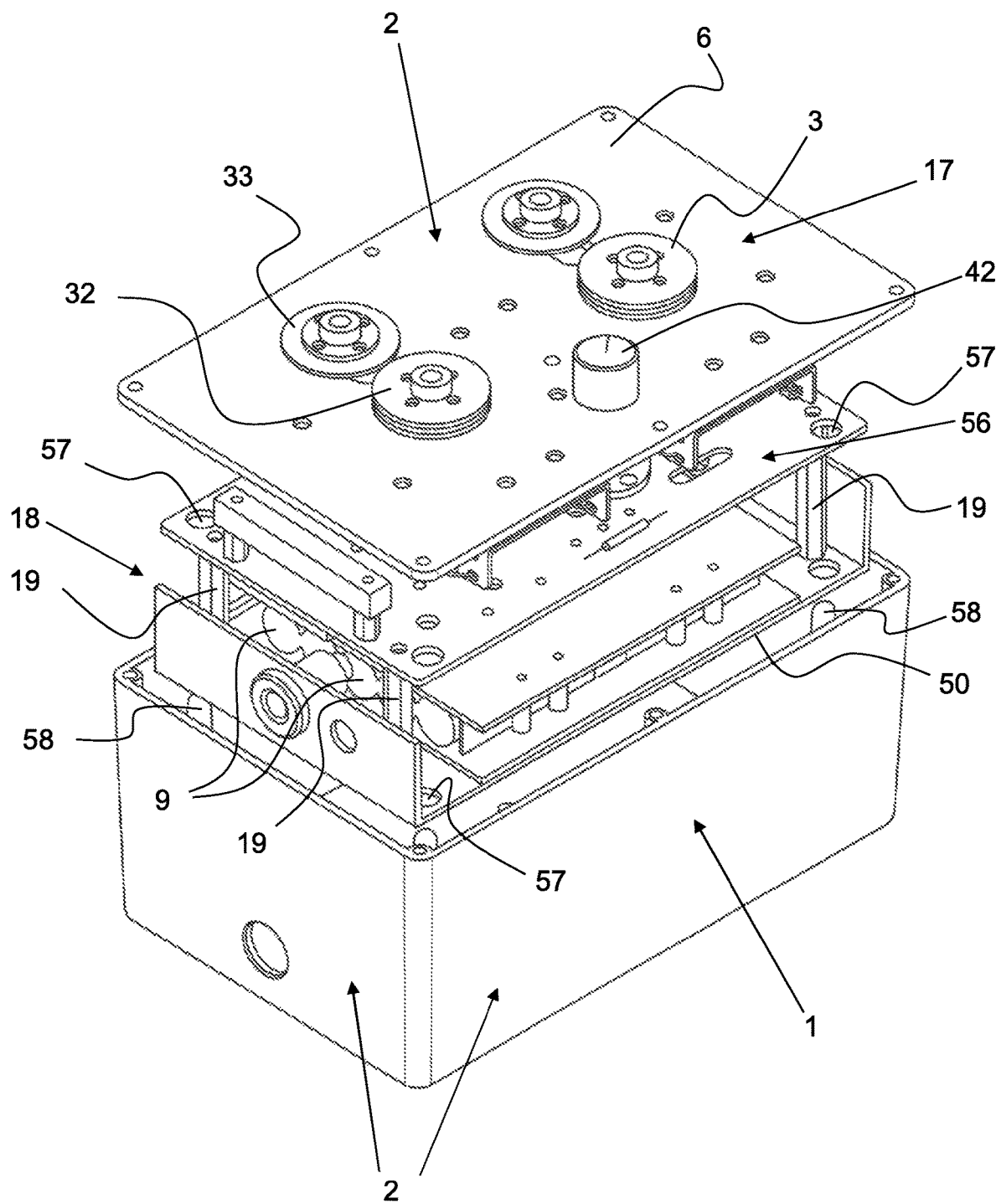
FIG. 4: The device according to FIG. 1 in an exploded drawing viewed from obliquely above, with cover plate, drive unit insertable in the housing and the housing at the bottom.

FIG. 3 shows this cover plate 17 viewed from its underside. The shaft 5 of the drive wheel, in the left half of the image, carries on this side a transmission wheel 25 with axially projecting cams 46, which is firmly connected to the shaft, wherein the shaft 5 is mounted fixedly in the cover plate 17. In contrast, the shaft 7 of the contact wheel 6 passes through the cover plate 17 in a recess 27 and is mounted in a slide 28, which is displaceable on this visible underside of the cover plate 17 in two opposite slots 59, which are formed by the two guide plates 51, 52, which are mounted on the cover plate 17 with some distance to the surface thereto. The slide 28 is connected to a support 54 which is connected on both sides of the shaft 7 to the end of two tension springs 29, wherein the other ends of the tension springs 29 are attached to a stationary support 53 at the underside of the cover plate 17. Thus the axis or shaft 7 of the contact wheel 6 can be moved away from the shaft 5 of the drive wheel 3 with one finger against the force of the two tension springs 29, as shown. The shaft 26 of the contact wheel 33 for the measuring wheel in the right half of the image is mounted in a slide 28 in exactly the same way and can be displaced against the force of tension springs 29. Below the measuring wheel the driving wheel 15 with its cams 46 can be recognized, which transmits its force to a wheel on the drive unit 18 (FIG. 4). The axis belonging to the rotary knob 42 carries a disc 55 with a contact element 48 on the underside of the cover plate 17 to switch the drive unit 18 on and off.

FIG. 4 shows the device in an exploded view from diagonally above, with cover plate 17, drive unit 18 insertable into housing 1 and housing 1 below. The drive unit 18 is arranged on a base plate 50, on which the batteries 9 for an electric motor are accommodated, as well as the necessary electronic control components for the electric motor and the management of the power supply. At the underside of a further mounting plate 56 of the drive unit 18, which is arranged on spacer supports 19 at the top, there is the electric motor, its drive axle with subsequent reduction gear and the electronic components for converting the rotation of the measuring wheel 32 into an electric signal. On the upper side of the mounting plate 56 there are further components which are shown and described in a separate view. This entire drive unit 18 can be countersunk in housing 1. For this purpose, guide pins 58 are used here on the bottom of the housing, over which the lower base plate 50 and the mounting plate 56 with their holes 57 can be placed, and afterwards the cover plate 17 is put on top of the housing 1 and screwed onto it at its corners, including the entire drive unit 18. The cover plate 17 with its mechanical components as well as the empty housing 1 can thus be sterilized before each new application by heating them to 180° C. in a sterilizing device. In the process, they cannot be damaged because they do not contain any temperature-sensitive parts. Afterwards the non-sterile drive unit 18, which cannot be sterilized due to its temperature-sensitive electronic and electric components, is inserted into the housing 1 and screwed tightly onto the cover plate 17, after which the device is sterile in its entirety because all external surfaces 2 and components are sterilized.

Figure 5:
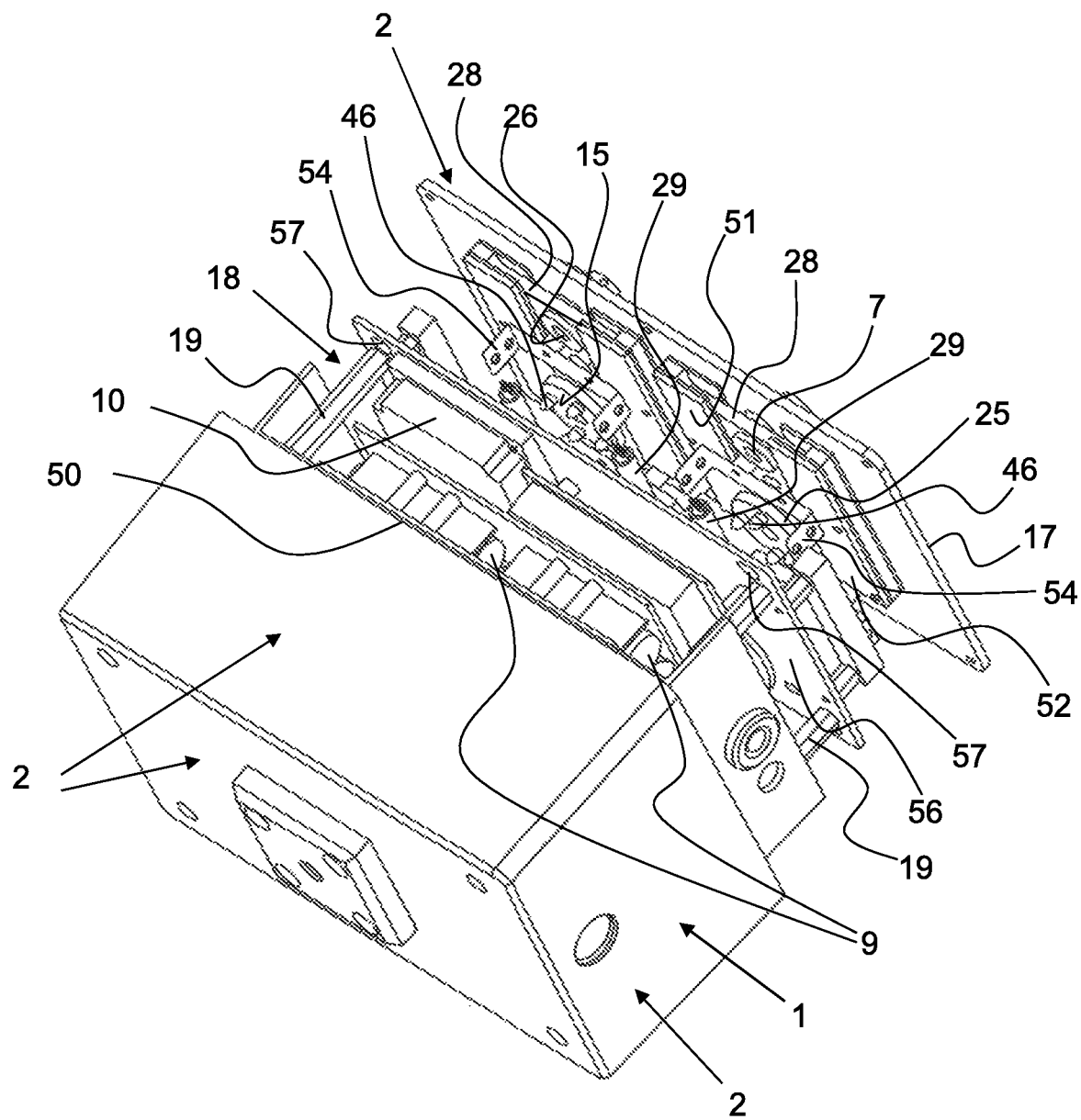
FIG. 5: The device according to FIG. 4 in an exploded drawing viewed from obliquely below, with cover plate, drive unit insertable in the housing and the housing at the bottom.

FIG. 5 shows the device as shown in FIG. 4 in an exploded view from below, with cover plate 17, drive unit 18 insertable into housing 1 and housing 1 below. On the underside of the cover plate 17 one recognizes the transmission wheels 25 with their protruding cams 46. Another drawing shows how the driving force is transferred from the drive unit 18 to the transmission wheel 25, and in the opposite direction the rotation of the measuring wheel 32 via the driving wheel 15 to the counting wheel in the drive unit 18. This solution enables the extremely simple removal and re-installation of the drive unit 18 for purposes of sterilization. The empty housing 1 and the cover plate 17 with their purely mechanical components can be sterilized before each use and afterwards the drive unit 18 can simply be put back into the housing 1 and the cover plate 17 screwed onto it.

Here in FIG. 5, one looks at the guide plates 51, 52 on the underside of the cover plate 17 for holding and guiding the slide 28, in which the displaceable shaft 7 for the contact wheel is mounted. The slide 28 also carries the movable holder 54 for the tension springs 29 for the return of the displacement after releasing the contact wheel and its shaft 7. In exactly the same way the displaceability of shaft 26 of the contact wheel for the measuring wheel is solved, as one recognizes on the left side of the image. Below the measuring wheel, this drives a driving wheel 15 with its cams 46.

Below the cover plate 17 one recognizes the drive unit 18. Below the mounting plate 56 there is the electronics 10 for the control of the electric motor and for the management of the power supply, which consists of a package of batteries 9. This whole drive unit 18 is presented and described in more detail in further images. It can be lowered into the housing 1 as a complete unit by putting it over guide pins in the housing 1 with its holes 57 at the corners in its base plate (not visible here) and in the mounting plate 56. Afterwards, the cover plate 17 can be screwed onto the housing 1, completely enclosing the drive unit 18 and the entire device, i.e. all its outward-facing parts 2 and walls are then sterile.

Figure 6:
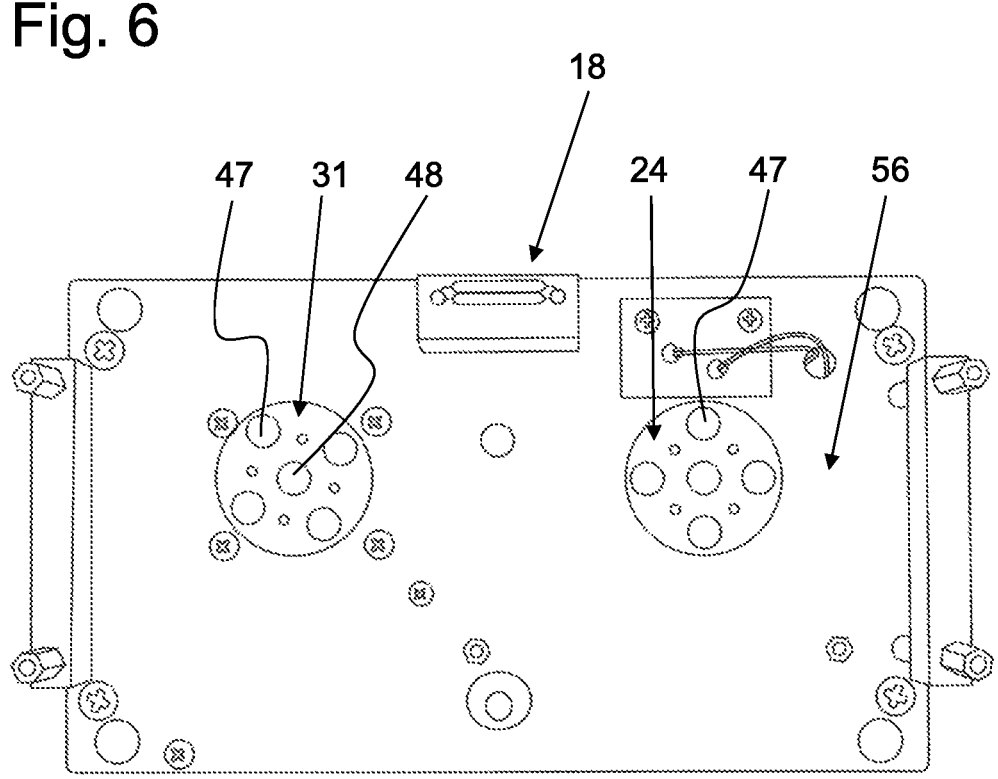
FIG. 6: The upper mounting plate of the drive unit of the device viewed from above.

FIG. 6 shows the upper side of the mounting plate 56 of the drive unit 18. The wheel on the right side is the driving wheel 24, which is driven by a gear by the electric motor below the mounting plate 56. It serves to transmit the driving force to the transmission wheel 25 at the underside of the cover plate 17. In contrast, the pick-up wheel 31 in the left half of the picture is used in the opposite direction to transmit the driving force which originates from the measuring wheel and its driving wheel 15. The measuring wheel on top of the cover plate 17 is driven by the fiber optic cable when it is driven by the drive wheel 3 and thus pulled through between the measuring wheel 32 and its contact wheel 33. The driving wheel 15 of the measuring wheel 32 transmits its driving force further downwards to this pick-up wheel 31 shown here by the cams 46 on the driving wheel 15 engaging in the holes 47 in the pick-up wheel 31 in a torque-locked manner. The pick-up wheel 31 passes the rotation on to a counting disc 12 underneath the mounting plate 56. Now it is clear how the underside of the cover plate 17 can be placed on this upper side of the mounting plate 56, namely in such a way that the cams 46 on the wheels on the underside of the cover plate 17 engage with the holes 47 on the wheels 24, 31 on the upper side of the mounting plate 56 in a torque-locked manner, namely the driving wheel 15 and the pick-up wheel 31 of the measuring wheel.

Figure 7:
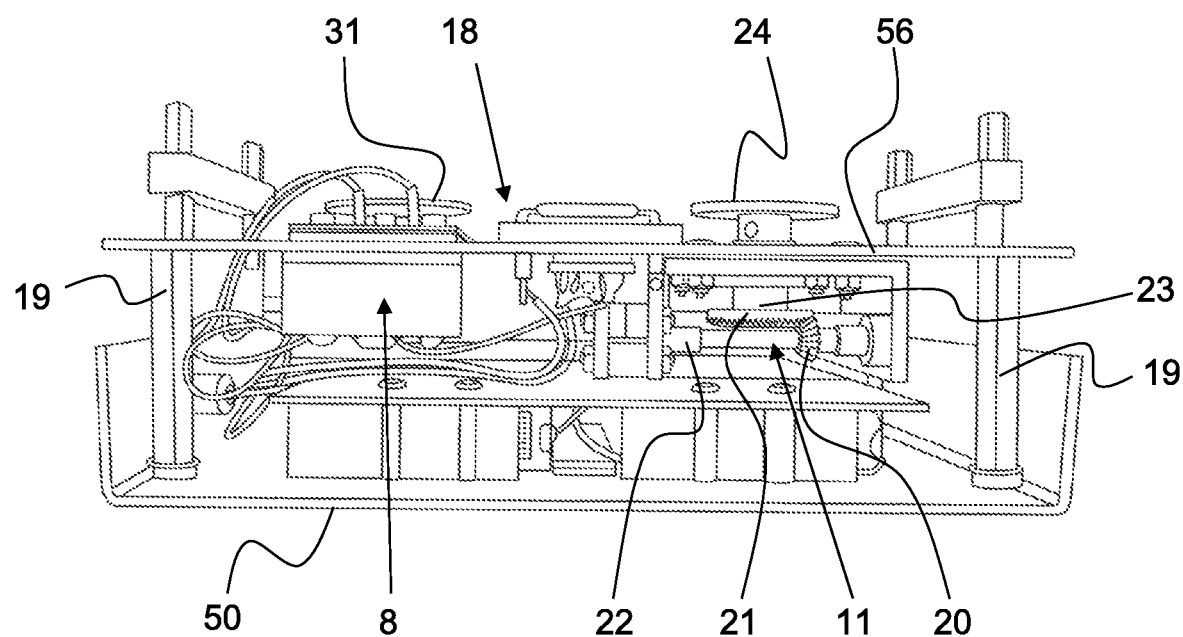
FIG. 7: The drive unit of the device viewed from the side.

FIG. 7 shows the entire drive unit 18 viewed from the side, with the mounting plate 56 at the top and the base plate 50 at the bottom. The electric motor 8 with its output shaft 22 and a bevel gear 20 at its end are installed at the bottom of the mounting plate 56. This bevel gear wheel 20 engages a gear wheel 21 which rotates with the shaft 23, on which the driving wheel 24 sits above the mounting plate 56. This forms a reduction gear 11 with a high reduction ratio, so that the shaft 23 can rotate very slowly and with a strong torque. The torque generated at the driving wheel 24 is finally transmitted to the drive wheel 3 via the engaging cams 46 of the transmission wheel 24. In the opposite direction, the force flows from the measuring wheel down to the pick-up wheel 31, which drives a counting disc, as will be shown.

Figure 8:
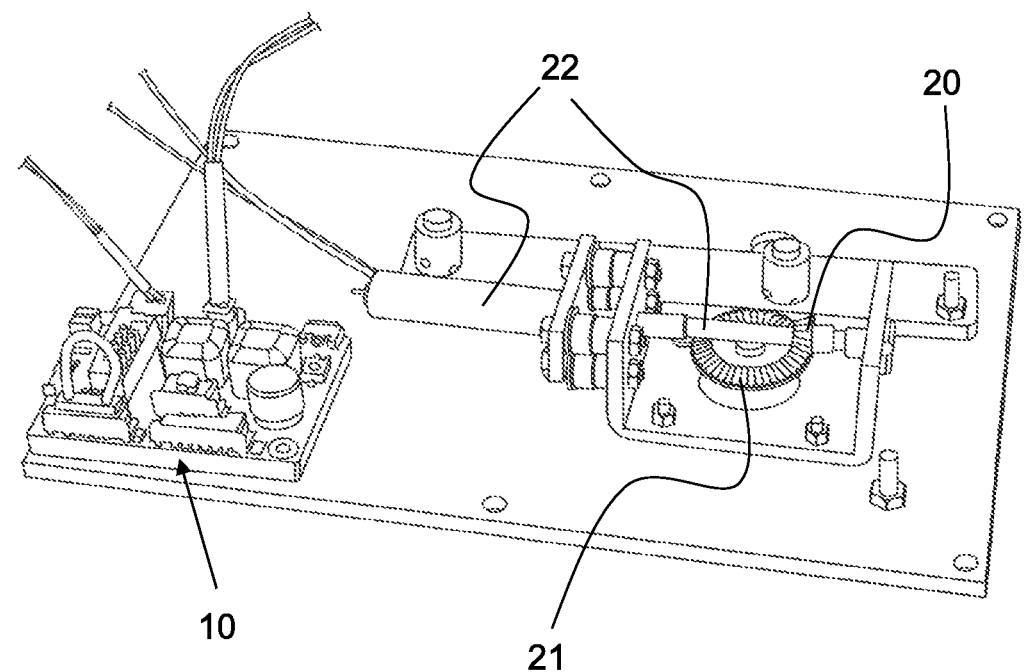
FIG. 8: The upper mounting plate of the drive unit of the device in an upside down position, viewed onto its underside in perspective.

FIG. 8 shows the underside of the mounting plate 56 with the output shaft 22 of the electric motor (not shown here), as well as the bevel gear 20 and the gear 21 driven thereby, the shaft of which ultimately drives the drive wheel 24 on the outside of the drive unit 18. The electronic control 10 with its components is also mounted on the mounting plate 56.

DETAILED DESCRIPTION

Figure 9:
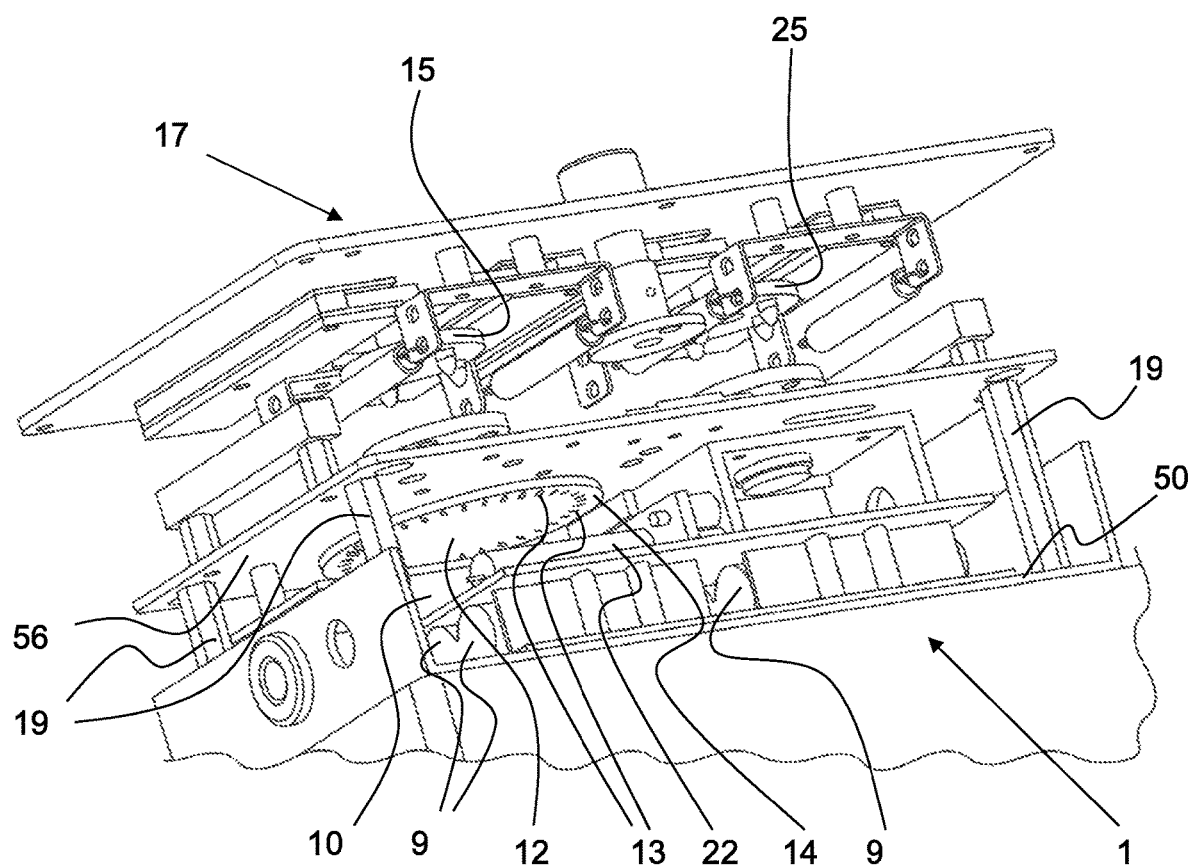
FIG. 9: The cover plate placeable on the housing viewed from below, therebelow the upper mounting plate of the drive unit and therebelow the housing viewed obliquely from below.

FIG. 9 discloses how the measurement of the conveying speed is realized. At the bottom of the mounting plate 56, a counting disc 12 rotates with the rotation of the measuring wheel. The counting disc 12 has radial slots 13 or holes in its circumferential area 14. Perpendicular to the counting disc 12, a light barrier is set up whose light beam passes through the hole area of the counting disc 12 and hits a light sensor on the other side. The number of incoming light pulses per time allows the associated electronics to determine the conveying speed of the fiber optic cable. The corresponding electric signal is supplied to the control unit 16 via cable 37 (FIG. 1). If the speed becomes zero due to a blockage, this control device 16 immediately interrupts the power supply to the laser to avoid burns in the vein. When a previously selected conveying length has been completed, the conveyor stops and the control device 16 generates a signal tone.

Figure 10:
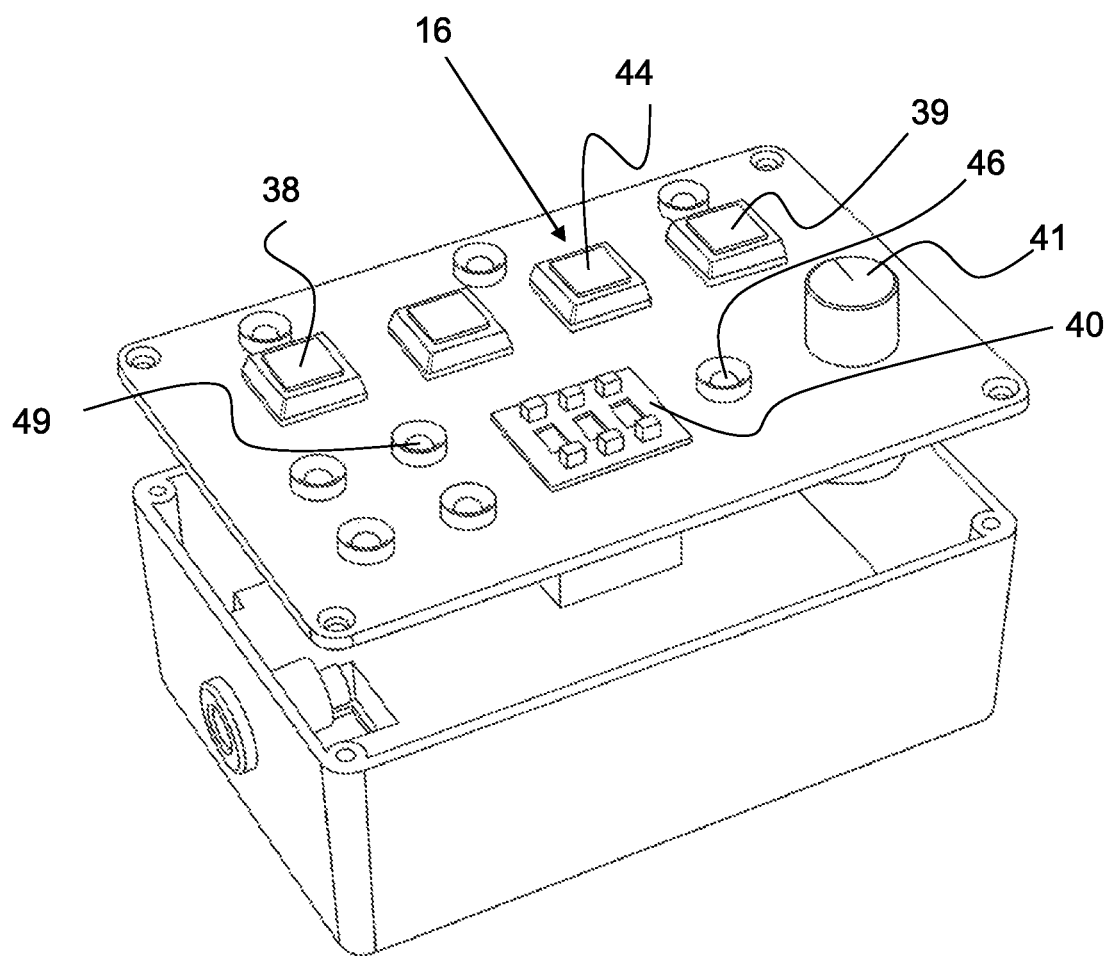
FIG. 10: The control device belonging to the device with upward removed cover having the control keys.

FIG. 10 shows the separate control device 16, which can be placed one or more meters away from the actual device for conveying the fiber optic cable and therefore does not necessarily have to be sterile and cannot be sterilized due to its electronic components. Otherwise, it would have to be placed in a sterile plastic container so that its buttons could be operated from the outside through the sterilizable plastic container. With this control device 16, at least the following functions can be switched and implemented by means of the electronic control 10 in the drive unit 18:

Switching the device on and off to connect or disconnect the power supply, and switching on the laser for the counting disc 21
Rotary knob 41 for stepless or discrete selection of the conveying speed of the cable 43
Display of the selected conveying speed of the fiber optic cable on the control device 16
Selection of a conveying length to be covered
Ready light, indicates device is ready to start conveying
Start button 38 for starting the conveying
Stop button 39 for stopping the conveying
Display 40 of the traveled conveying length
Restart button 44 for zeroing the displayed conveying path
Indicator 49 of battery charge when powered by batteries
Automatic shutdown of the catheter laser upon stop of the delivery. For this purpose, a control cable which is not shown leads to the generator for the laser.
A signal tone is emitted when the conveying length is complete.

NUMERICAL INDEX

1 Housing
2 Outer side of the device
3 Drive wheel
4 Circumferential area drive wheel 3
5 Shaft of drive wheel 3
6 Contact wheel
7 Shaft of contact wheel 6
8 Electric motor
9 Power supply electric motor 8
10 Electronic control
11 Reduction gear for drive wheel 3
12 Counting disc
13 radial slots in the counting wheel 12
14 Circumferential area of the counting disc
15 Drive wheel of contact wheel 32
16 Control device
17 Cover plate
18 Drive unit
19 Spacer supports in the drive unit
20 Bevel gear
21 Gear
22 Shaft of drive wheel at the electric motor 8
23 Shaft drive wheel at the drive unit 18
24 Drive wheel outside on the drive unit 18
25 Transmission wheel
26 Shaft of contact wheel 33
27 Recess in the cover plate for the displacement of the contact wheel
28 Slide at the underside of the cover plate
29 Springs for the contact wheel
30 Shaft of contact wheel 32
31 Pick-up wheel
32 Measuring wheel outside on the cover plate 14
33 Contact wheel for the measuring wheel 32
34 Driving wheel
35 Pick-up wheel for the driving wheel 34
36 Shaft of pick-up wheel 35
37 Electric cable
38 Start button
39 Stop button
40 Display of the traveled conveying length
41 Rotary knob for regulating conveying speed
42 Rotary knob as a main switch of energy supply
43 Cable to be conveyed
44 Restart button
45 Ready light
46 Cams
47 Recesses for nubs
48 Contact element on washer 55
49 Battery charge indicator
50 Base plate drive unit 18
51 Guide plate for slide 28
52 Guide plate for slide 28
53 Stationary holder for springs 29

54 Adjustable mount on the slide for the springs 29
55 Disk at the bottom of the knob
56 Mounting plate
57 Guide holes
58 Guide mandrels on housing bottom
59 Slots for the slide

The invention claimed is:

1. A device for the controlled conveying of a cable in the form of a catheter having a light guide or a glass fiber or of an electric cable or of a cable-like tubelet, the device comprising: a drive wheel and a contact wheel which can be pressed radially onto the drive wheel, between which the cable to be conveyed can be clamped, so that it is conveyable by the drive of the drive wheel of a drive unit having an appurtenant control unit comprising electronic controls with a measuring device for measuring the rotational motion and rotational speed of the drive wheel,
wherein the device is designed in three parts, having firstly a cover plate on whose outer side are externally mounted the drive wheel and the contact wheel which can be radially pressed onto said drive wheel, wherein the cover plate, the drive wheel, and the contact wheel can be sterilized by heating to at least 180° C., secondly a non-sterilizable drive unit having an electronic control, an electric motor, a reduction gear and a power supply, and thirdly a box-shaped housing which can also be sterilized by heating to at least 180° C. and into which the drive unit can be completely inserted and can be closed sterilely with the sterilized cover plate so that the device is completely sterile on its outside on all sides, and a separate appurtenant control unit which can be connected to the sterilized device via an electric cable.

2. The device according to claim 1, wherein the rotational motion of the drive wheel is transmitted to a counting disc running synchronously therewith, having radial slots or holes in the circumferential area, which is rotatable by a stationary light barrier, for determining the motion and rotational speed of the drive wheel.

3. The device according to claim 1, wherein the housing has on its outer side a drive wheel, having the contact wheel which acts on its circumferential surface in the radial direction thereto and is displaceable at right angles to its axis, having an axis mounted parallel to that of the drive wheel, so that the cable can be clamped between the drive wheel and the contact wheel for conveying purposes, and that the drive unit has inside the housing an electric motor having an appurtenant power supply and electronic control, by which the drive wheel can be driven via a reduction gear, and that a counting disc having radial slots or holes is present inside the housing in its circumferential area, through which a stationary light barrier can pass, for detecting motion and rotational speed of the counting disc of the measuring device and thus of the drive wheel, for generating electric signals for the processing and display of on an associated control unit which can be connected by an electric cable and from which the the device can be controlled.

4. The device according to claim 1, wherein the electric motor is connected inside the drive unit with its output axis to a shaft which carries a bevel gear which is in engagement with a gear wheel on the shaft of the drive wheel located outside on the drive unit, which in turn can be brought into torque-locking coupling with a transmission wheel on the underside of the cover plate, wherein this transmission wheel is seated on the shaft of the drive wheel located outside the cover plate.

5. The device according to claim 4, wherein the drive wheel carries a transmission wheel outside on the cover plate with its shaft at the underside of the cover plate, for torque-locking coupling to the drive wheel above the drive unit upon placing the cover plate on the housing.

6. The device according to claim 4, wherein the torque-locking connection of the driving wheel to the transmission wheel is realized by an axial engagement of the same, just as the torque-locking connection of the driving wheel on the underside of the cover plate to a pick-up wheel on the upper side of the drive unit, which carries a counting disc with its shaft inside the drive unit.

7. The device according to claim 6, wherein the torque-locked connection of the driving wheel to the transmission wheel and the torque-locked connection of the driving wheel to the pick-up wheel are realized by the fact that respectively one wheel has axial cams which, upon the cover plate being placed on the housing, engage in recesses in the adjoining wheel.

8. The device according to claim 1, wherein the displaceable contact wheel belonging to the drive wheel outside the cover plate has a shaft which passes through the cover plate in a recess, and this shaft is guided displaceably on a slide away from the drive wheel against the force of springs on the underside of the cover plate.

9. The device according to claim 1, wherein a freely rotating measuring wheel having a shaft is mounted on the cover plate parallel to the shaft of the drive wheel, with its own spring-loaded contact wheel like that contact wheel to the drive wheel, and in that the shaft of the measuring wheel on the underside of the cover plate carries a driving wheel for a pick-up wheel on the upper side of the drive unit, to which driving wheel it can be torque-lockingly coupled upon placing the cover plate on the housing, and which pick-up wheel carries a counting disc with its shaft in the interior of the drive unit.

10. The device according to claim 1, wherein the device and its electronic control can be operated via an electric cable by a remote control device.

11. The device according to claim 1, wherein the power supply is ensured by a number of rechargeable batteries inside the drive unit, which can be charged via the electric cable.

12. The device according to claim 1, wherein using the control device and the electronic control connected thereto in the drive unit at least the following functions can be switched and actionable:
Switching the device on and off to connect or disconnect the power supply, and switching on the laser for a counting disc
Rotary knob for stepless or discrete selection of the conveying speed of the cable
Selection of the conveying length to be covered
Ready light for starting the device
Display of the selected conveying speed at the control unit
Start button for starting the conveying
Stop button for stopping the conveying
Display of the travelled conveying length
Restart button for zeroing the displayed conveying path
Indicator of battery charge when powered by batteries
Automatic shutdown of a catheter laser when the delivery is stopped via control cable to the generator of a laser
Stopping the conveyor when the selected conveying length has been covered and emitting a signal tone.

* * * * *